United States Patent
Shi et al.

(10) Patent No.: US 11,931,280 B2
(45) Date of Patent: Mar. 19, 2024

(54) CONNECTING AND RELEASING STRUCTURE FOR BALLOON SYSTEM

(71) Applicants: Changzhou Panda Medical Co., Ltd., Suzhou (CN); Shanghai Panda Medical Co., Ltd., Shanghai (CN)

(72) Inventors: Xiufeng Shi, Shanghai (CN); Qiang Zhang, Shanghai (CN)

(73) Assignees: Changzhou Panda Medical Co., Ltd., Jiangsu (CN); Shanghai Panda Medical Co., Ltd., Shanghai (CN)

( * ) Notice: Subject to any disclaimer, the term of this patent is extended or adjusted under 35 U.S.C. 154(b) by 423 days.

(21) Appl. No.: 16/765,119

(22) PCT Filed: Dec. 4, 2018

(86) PCT No.: PCT/CN2018/119123
§ 371 (c)(1),
(2) Date: May 18, 2020

(87) PCT Pub. No.: WO2019/120072
PCT Pub. Date: Jun. 27, 2019

(65) Prior Publication Data
US 2020/0345528 A1    Nov. 5, 2020

(30) Foreign Application Priority Data

Dec. 18, 2017 (CN) .......................... 201711367602.0

(51) Int. Cl.
*A61F 5/00* (2006.01)
*A61M 25/10* (2013.01)

(52) U.S. Cl.
CPC ............ *A61F 5/0089* (2013.01); *A61F 5/003* (2013.01); *A61F 5/0036* (2013.01); *A61M 25/1029* (2013.01)

(58) Field of Classification Search
CPC ...... A61F 5/0033; A61F 5/0036; A61F 5/004; A61F 5/0043; A61F 5/0056;
(Continued)

(56) References Cited

U.S. PATENT DOCUMENTS

| 5,993,473 A | 11/1999 | Chan et al. |
| 8,974,483 B2 * | 3/2015 | Gaur ...................... A61F 5/0036 623/23.65 |

(Continued)

FOREIGN PATENT DOCUMENTS

| CN | 204890270 | 12/2015 |
| CN | 108158705 | 6/2018 |

(Continued)

*Primary Examiner* — Sarah A Long
*Assistant Examiner* — Lindsey Bachman
(74) *Attorney, Agent, or Firm* — Dentons US LLP (57) ABSTRACT

The present application provides a connecting and releasing structure for a balloon system, a balloon system comprising the connecting and releasing structure, and a method for fabricating the same. The connecting and releasing structure is used for connection and release of a catheter and a balloon. The connecting and releasing structure comprises a self-sealing valve positioned on the balloon. The self-sealing valve comprises a catheter connecting port. The catheter passes through the catheter connecting port and is sealedly connected to the self-sealing valve. The self-sealing valve is completely or partially bonded to the inner wall of the balloon. When the catheter is removed after delivery of a filler, the self-sealing valve is not pulled out of the balloon, and thus leakage of the filler can be prevented. In addition, the perimeter of a small orifice in a side wall of the self-sealing valve or the perimeter of the cross-section of the distal end thereof is not greater than the outer diameter of the catheter, and therefore, no leakage occurs when the balloon is full of filler. In addition, the perimeters of cross-sections of the self-sealing valve may differ and increase gradually or (Continued)

stepwise from distal to proximal, thus facilitating the insertion and removal of the catheter.

12 Claims, 5 Drawing Sheets

(58) Field of Classification Search
CPC .. A61F 5/0089; A61F 2/441; A61F 2002/501; A61M 25/1018; A61M 25/10185; A61M 25/1025; A61M 2025/1054; A61M 2039/064–066; A61B 17/7097; A61B 17/8855

See application file for complete search history.

(56) References Cited

U.S. PATENT DOCUMENTS

| | | | |
|---|---|---|---|
| 2003/0171768 A1* | 9/2003 | McGhan | A61F 5/003 606/191 |
| 2009/0270985 A1* | 10/2009 | Schuessler | A61F 5/0036 623/8 |
| 2013/0226219 A1 | 8/2013 | Brister et al. | |
| 2016/0120653 A1* | 5/2016 | Hibri | A61F 2/441 29/525.01 |

FOREIGN PATENT DOCUMENTS

| EP | 1929957 A1 | 6/2008 |
|---|---|---|
| WO | 2009059802 A1 | 5/2009 |

* cited by examiner

CONNECTING AND RELEASING STRUCTURE FOR BALLOON SYSTEM

This application is the National Stage filing under 35 U.S.C. 371 of International Application No. PCT/CN2018/119123, filed on Dec. 4, 2018, which claims priority to Chinese Application No. 201711367602.0, filed on Dec. 18, 2017, the contents of which are all hereby incorporated by reference herein in their entirety.

FIELD OF THE INVENTION

The present application relates to an implantation system. In particular, it relates to a connecting and releasing structure for a balloon implantation system.

BACKGROUND OF THE INVENTION

During the past 20 years, the incidence of obesity, including adult obesity, geriatric obesity, and adolescent and paediatric obesity, has sky-rocketed globally. According to WHO global statistics, 15% of adult females and 11% of adult males were obese in 2014. This means that in 2014 nearly one billion of the world's adults were obese. Disturbingly, China's obese population has surpassed the US. In 2016, there were 89.60 million obese people in China (87.80 million in the US), of which 43.20 million were male and 46.40 million female. Obesity is generally accompanied by hypertension, type-II diabetes, ischemic heart disease, dyslipidaemia, joint degeneration, sleep apnoea, and certain tumours. Therefore, the question of how to effectively control bodyweight and prevent and control complications is a topic of concern.

At present, dietary restrictions, life interventions, drug therapies, and surgical treatments are the main ways to treat obesity. However, it is difficult to achieve satisfactory weight-loss results by relying simply on dietary restrictions, life interventions, and drug therapies. Although the effectiveness of weight-loss surgery is obvious, patients are resistant to accepting this approach for reasons relating to culture, medical standards, and surgery-related complications. Implanted medical device weight loss, which simulates the mechanisms of surgical treatment of obesity and includes intragastric balloons, has emerged in recent years. Being safe, effective, and reversible, it has received wide attention and is likely to become the main effective means of weight reduction.

There are already several types of intragastric balloons being marketed abroad. In particular, intragastric balloons which can be swallowed without gastroscopic delivery constitute the weight-loss method of the future. Ingested intragastric balloons are enclosed in a gelatin capsule prior to administration and are connected to a relatively long catheter. One end of the catheter is connected to a self-sealing valve on the intragastric balloon, and the other end remains outside the capsule and the oral cavity. The balloon enclosed in the capsule and a portion of the catheter is delivered by means of swallowing into the patient's stomach, where the capsule is rapidly degraded in the gastric acid environment. A filler is delivered from the extracorporeal end of the catheter, which was left outside the patient's oral cavity, into the balloon. The balloon undergoes a transition from an initial decompressed state to an inflated state. After all the filler has been delivered, the catheter is removed from the patient's body.

The self-sealing valve that is on the balloon and that forms a fluid passage to the catheter automatically closes to prevent the filler from leaking. U.S. Pat. No. 8,974,483 B2 discloses such a connecting and releasing structure for a catheter and a balloon. For the particulars, refer to FIG. 1.

Figure 1:
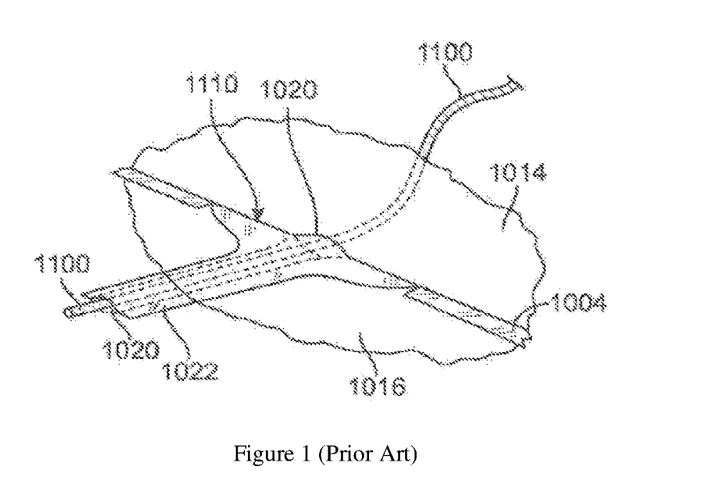
FIG. 1 is a diagram of a balloon sealing structure according to the prior art.

This type of connecting and releasing structure for a catheter and a balloon disclosed by U.S. Pat. No. 8,974,483 B2 includes a catheter 1100 and a two-layer self-sealing valve 1110 that is sealed along its edges. The self-sealing valve 1110 may be positioned in an orifice in the upper 1014 or lower 1016 surface material of the balloon or in an opening in a seam 1004 of the upper 1014 and lower 1016 material. From outside the balloon, the catheter 1100 enters the balloon via a passage 1020 through the two-layer self-sealing valve 1110. After it completes delivery of filling material into the balloon, the catheter 1100 is removed, and the path 1020 through the two-layer self-sealing valve 1110 automatically closes to prevent leakage of filler from inside the balloon.

The defect of this type of structure is the following: if the perimeter of a cross-section of the catheter is greater than or equal to a cross-section perimeter of the passage 1020, the two-layer self-sealing valve 1110 is likely to be pulled out of the balloon when the catheter 1100 is removed upon filling the balloon, resulting in leakage of the filler. On the other hand, if the perimeter of a cross-section of the catheter 1100 is smaller than a cross-section perimeter of the passage 1020, filler is likely to leak out of the balloon through a gap between the catheter 1100 and the passage 1020 when the balloon is filled, resulting in self-sealing failure.

Therefore, the matter of how to design a self-sealing structure with better sealing performance, such that it has a very good seal that prevents filler leakage both during the delivery of the filler by the catheter and after removal of the catheter from the balloon, is a problem in urgent need of solution in the art.

SUMMARY OF THE INVENTION

To solve the technical problem described above, the present application provides a new connecting and releasing structure for a catheter and a balloon. This connecting and releasing structure causes a very good seal that prevents filler leakage both during the delivery of the filler by the catheter and after removal of the catheter from the balloon.

A connecting and releasing structure for a balloon system is provided according to an aspect of the present application. The connecting and releasing structure is for connecting and releasing a catheter and a balloon. The connecting and releasing structure comprises a self-sealing valve positioned on the balloon. The self-sealing valve comprises a catheter connecting port. The catheter passes through the catheter connecting port and is sealedly connected to the self-sealing valve. It is characterised in that the self-sealing valve is secured to the inner wall of the balloon.

Furthermore, the self-sealing valve comprises a passage lumen positioned inside the balloon. A first end of the self-sealing valve is sealedly connected to an opening on the balloon. The catheter enters the self-sealing valve from the first end, exits the catheter connecting port, and enters the interior of the balloon.

In an embodiment, the catheter connecting port may be disposed in a small orifice on a side wall of the self-sealing valve. The perimeter of this small orifice is no greater than the outer diameter of the catheter.

Furthermore, the distal end of the self-sealing valve is bonded to the inner wall of the balloon.

Optionally, all of the side of the self-sealing valve that does not contain a small orifice is bonded to the inner wall of the balloon.

In an embodiment, the balloon comprises a balloon upper layer and a balloon lower layer. An inversion hole is disposed on the balloon upper layer. The self-sealing valve comprises a self-sealing valve upper layer connected to the balloon upper layer and a self-sealing valve lower layer connected to the balloon lower layer, wherein a small orifice is opened in the self-sealing valve upper layer, and the perimeter of the small orifice is no greater than the outer diameter of the catheter. The balloon upper layer and self-sealing valve upper layer are combined with the balloon lower layer and the self-sealing valve lower layer by connecting them along their edges to form an integral structure. After they are combined, they are inverted through use of the inversion hole on the balloon upper layer. The balloon upper layer and the balloon lower layer form the balloon, and the self-sealing valve upper layer and the self-sealing valve lower layer form the self-sealing valve positioned inside the balloon. The self-sealing valve is secured to the inner wall of the balloon, and the inversion hole on the balloon upper layer is sealed with a patch.

Furthermore, the distal end of the self-sealing valve upper layer and/or the self-sealing valve lower layer is bonded to the inner wall of the balloon.

Optionally, all of the self-sealing valve lower layer is bonded to the inner wall of the balloon.

Furthermore, the self-sealing valve upper layer and the balloon upper layer are formed entirely from the same type of material or are connected together by bonding or welding different materials.

Furthermore, the self-sealing valve lower layer and the balloon lower layer are formed entirely from the same type of material or are connected together by bonding or welding different materials.

A method for fabricating the aforesaid connecting and releasing structure for a balloon system is provided according to another aspect of the present application. It comprises the steps below: providing a balloon upper layer, a balloon lower layer, a self-sealing valve upper layer connected to the balloon upper layer, and a self-sealing valve lower layer connected to the balloon lower layer; disposing an inversion hole on the balloon upper layer; opening a small orifice on the self-sealing valve upper layer, the perimeter of the small orifice being no greater than the outer diameter of the catheter; combining the balloon upper layer and the self-sealing valve upper layer with the balloon lower layer and the self-sealing valve lower layer by connecting them along their edges to form an integral structure; after they are combined, using the inversion hole on the balloon upper layer to invert them; the balloon upper layer and the balloon lower layer forming a balloon, and the self-sealing valve upper layer and the self-sealing valve lower layer forming a self-sealing valve positioned inside the balloon; securing the self-sealing valve to the inner wall of the balloon, and sealing the inversion hole on the balloon upper layer with a patch.

Furthermore, the balloon upper layer and the self-sealing valve upper layer and the balloon lower layer and the self-sealing valve lower layer are combined by bonding or welding them along their edges.

Furthermore, the distal end of the self-sealing valve upper layer and/or self-sealing valve lower layer is bonded to the inner wall of the balloon.

Optionally, all of the self-sealing valve lower layer is bonded to the inner wall of the balloon.

Furthermore, the self-sealing valve is connected to the balloon by bonding or welding.

In another embodiment, the catheter connecting port is an opening formed in a distal second end of the self-sealing valve, and the perimeter of the opening is no greater than the outer diameter of the catheter.

Furthermore, all of the distal end or one side of the self-sealing valve is bonded to the inner wall of the balloon.

Furthermore, the perimeters of cross-sections of the self-sealing valve may differ and decrease gradually or stepwise from a first end to the second end, thus facilitating the insertion and removal of the catheter.

Furthermore, the self-sealing valve may be composed of two layers of material sealed along two edges, or it may be a seamless tubular material.

Furthermore, the face of the second end of the self-sealing valve is uneven.

In an embodiment, the balloon comprises a balloon upper layer and a balloon lower layer. An inversion hole is disposed on the balloon upper layer. The self-sealing valve comprises a self-sealing valve upper layer connected to the balloon upper layer and a self-sealing valve lower layer connected to the balloon lower layer. The balloon upper layer and the self-sealing valve upper layer are combined with the balloon lower layer and the self-sealing valve lower layer by connecting them along their edges to form an integral structure. However, the head of the self-sealing valve upper layer and the head of the self-sealing valve lower layer are not connected, and the perimeter of the opening formed by the head of the self-sealing valve upper layer and the head of the self-sealing valve lower layer is no greater than the outer diameter of the catheter. After the layers are combined, they are inverted through use of the inversion hole on the balloon upper layer. The balloon upper layer and the balloon lower layer form the balloon, and the self-sealing valve upper layer and the self-sealing valve lower layer form the self-sealing valve positioned inside the balloon. The self-sealing valve is secured to the inner wall of the balloon, and the inversion hole on the balloon upper layer is sealed with a patch.

Furthermore, the distal end or all of the self-sealing valve upper layer is bonded to the inner wall of the balloon, or the distal end or all of the self-sealing valve lower layer is bonded to the inner wall of the balloon.

Furthermore, the size of the head of the self-sealing valve upper layer and the head of the self-sealing valve lower layer is smaller than the end which is connected to the balloon, thus forming a conical self-sealing valve.

Furthermore, the self-sealing valve upper layer and the balloon upper layer are formed entirely from the same type of material or are connected together by bonding or welding different materials.

Furthermore, the self-sealing valve lower layer and the balloon lower layer are formed entirely from the same type of material or are connected together by bonding or welding different materials.

A method for fabricating the aforesaid connecting and releasing structure for a balloon system is provided according to another aspect of the present application. It comprises the steps below: providing a balloon upper layer, a balloon lower layer, a self-sealing valve upper layer connected to the balloon upper layer, and a self-sealing valve lower layer connected to the balloon lower layer; disposing an inversion hole on the balloon upper layer; combining the balloon upper layer and the self-sealing valve upper layer with the balloon lower layer and the self-sealing valve lower layer by connecting them along their edges to form an integral structure. However, the head of the self-sealing valve upper layer and the head of the self-sealing valve lower layer are not connected, and the perimeter of the opening formed by the head of the self-sealing valve upper layer and the head of the self-sealing valve lower layer is no greater than the outer diameter of the catheter. After the layers are combined, they are inverted through use of the inversion hole on the balloon upper layer. The balloon upper layer and the balloon lower layer form the balloon, and the self-sealing valve upper layer and the self-sealing valve lower layer form the self-sealing valve positioned inside the balloon. The self-sealing valve is secured to the inner wall of the balloon, and the inversion hole on the balloon upper layer is sealed with a patch.

Furthermore, the self-sealing valve is secured to the inner wall of the balloon by bonding the distal end or all of the self-sealing valve upper layer to the inner wall of the balloon, or the self-sealing valve is secured to the inner wall of the balloon by bonding the distal end or all of the self-sealing valve lower layer to the inner wall of the balloon.

Furthermore, the balloon upper layer and the self-sealing valve upper layer and the balloon lower layer and the self-sealing valve lower layer are combined by bonding or welding them along their edges.

Furthermore, the self-sealing valve is connected to the balloon by bonding or welding.

A balloon system is provided according to another aspect of the present application. It comprises the connecting and releasing structure described above.

In an embodiment, the balloon system is an intragastric balloon system.

In another embodiment, the balloon system is a skin expansion balloon.

According to the connecting and releasing structure of the present application, a self-sealing valve is wholly or partially bonded to the inner wall of a balloon. When the catheter is removed after delivery of a filler, the self-sealing valve is not pulled out of the balloon, and thus leakage of the filler can be prevented. In addition, the perimeter of a small orifice in a side wall of the self-sealing valve or the perimeter of the cross-section of the distal end thereof is not greater than the outer diameter of the catheter, and therefore, no leakage occurs when the balloon is full of filler. In addition, the perimeters of cross-sections of the self-sealing valve may differ and increase gradually or stepwise from distal to proximal, thus facilitating the insertion and removal of the catheter.

SPECIFIC EMBODIMENTS

The following is a clear and complete description of technical schemes among embodiments of the present application. Obviously, the described embodiments are only some of the embodiments of the present application and not all of the embodiments. So long as no creative work is expended, all embodiments made by persons with ordinary skill in the art from embodiments of the present application belong within the protected scope of the present application.

Figure 2:
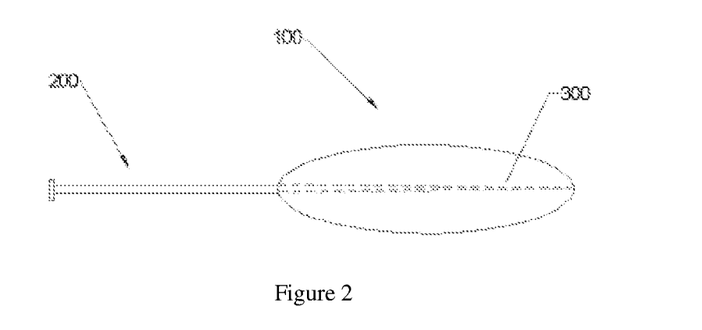
FIG. 2 is a structural diagram of a balloon system of an embodiment according to the present application.

Refer to FIG. 2, which is a structural diagram depicting a balloon system containing a connecting and releasing structure according to an embodiment of the present application. Preferably, this balloon system is a balloon system implanted in the human body, such as an intragastric balloon system. It would be easy for a person skilled in the art to see that the balloon system of the present application could be a balloon system used for other purposes, such as a skin expansion balloon. The implant balloon system includes: a balloon 100, a catheter 200, and a gelatin capsule and filler (not shown in the drawing). The balloon 100 contains a self-sealing valve 300. The balloon 100 is enclosed in the gelatin capsule before it is swallowed. One end (i.e., the intracorporeal end) of the catheter 200 is connected to the self-sealing valve 300 on the balloon 100. The other end (i.e., the extracorporeal end) remains outside the capsule. The catheter 200 is long enough that the extracorporeal end remains outside the oral cavity during use. Both the balloon and the self-sealing valve according to the present application are made from flexible materials.

Figure 3:
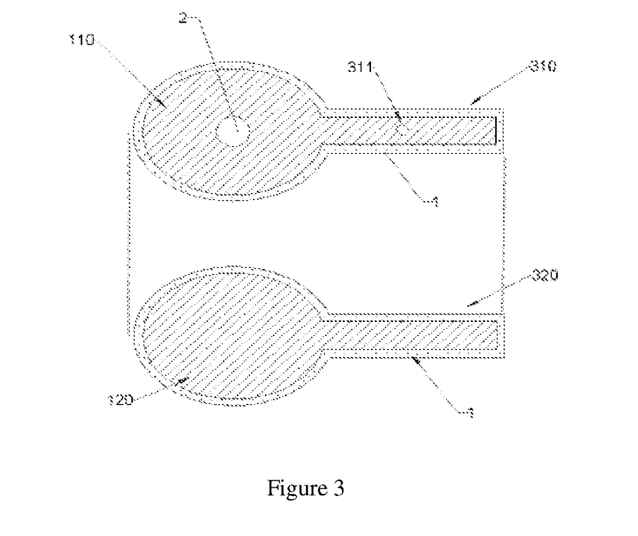
FIG. 3 is a balloon and a self-sealing valve according to an embodiment of the present application and an exploded view of the same.

FIGS. 3 through 6 depict an implant balloon system according to an embodiment of the present application. The structure and fabrication method of a balloon system of this embodiment are described in detail below with reference to FIGS. 3 through 6. This implant balloon system is specifically an intragastric balloon system. Refer to FIG. 3, which depicts the balloon 100, self-sealing valve 300, and an exploded view thereof. The self-sealing valve 300 has a side-wall opening. The balloon 100 comprises a balloon upper layer 110 and a balloon lower layer 120. An inversion hole 2 is disposed on the balloon upper layer 110. The self-sealing valve 300 comprises a self-sealing valve upper layer 310 connected to the balloon upper layer 110 and a self-sealing valve lower layer 320 connected to the balloon lower layer 120, wherein a small orifice 311 is opened in the self-sealing valve upper layer 310, and the perimeter of the small orifice 311 is no greater than the outer diameter of the catheter 200. The self-sealing valve upper layer 310 and the balloon upper layer 110 may be formed entirely from the same type of material or may be connected together by bonding or welding different materials. Likewise, the self-sealing valve lower layer 320 and the balloon lower layer 120 may be formed entirely from the same type of material or may be connected together by bonding or welding different materials. The balloon upper layer 110 and the self-sealing valve upper layer 310 are combined with the balloon lower layer 120 and the self-sealing valve lower layer 320 by connecting them along their edges 1 to form an integral structure. After they are combined, they are inverted through use of the inversion hole 2 on the balloon upper layer 110.

Figure 4:
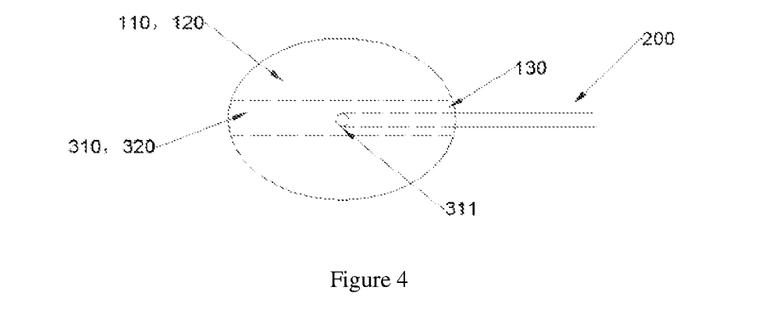
FIG. 4 is a top view of a catheter assembled with the self-sealing valve depicted in FIG. 3.

The balloon upper layer 110 and the balloon lower layer 120 form the balloon 100, and the self-sealing valve upper layer 310 and the self-sealing valve lower layer 320 form the self-sealing valve 300. The self-sealing valve 300 enters the interior of the balloon 100. Next, the distal end or all of the self-sealing valve upper layer 310 and the self-sealing valve lower layer 320 is bonded to the inner wall of the balloon 100, as shown in FIG. 4. Lastly, the inversion hole 2 on the balloon upper layer 110 is sealed with a patch.

Figure 5:
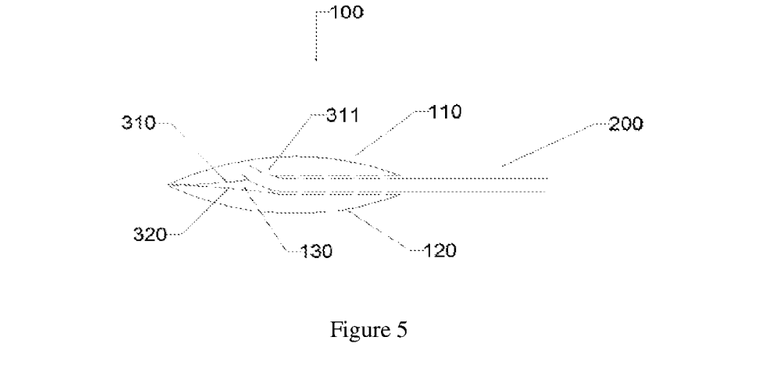
FIG. 5 is a side view of a catheter assembled with the self-sealing valve depicted in FIG. 3.

Refer to FIGS. 4 and 5. FIG. 4 is a top view of a catheter assembled with the self-sealing valve depicted in FIG. 3, and FIG. 5 is a side view of a catheter assembled with the self-sealing valve depicted in FIG. 3. The catheter 200 passes from outside the balloon 100 into the passage lumen 130 between the self-sealing valve upper layer 310 and the self-sealing valve lower layer 320 and passes out from the small orifice 311 on the self-sealing valve upper layer 310 and enters the interior of the balloon 100.

Figure 6:
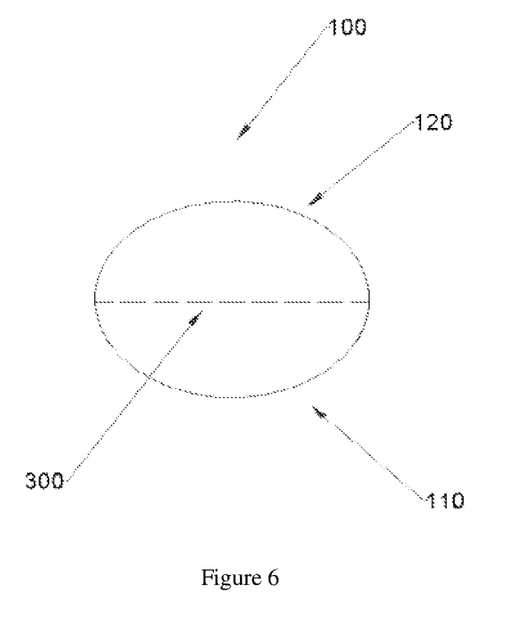
FIG. 6 is a side view of the balloon after the catheter was removed from the self-sealing valve depicted in FIG. 3.

The intragastric balloon according to the present embodiment is used as follows: after the patient swallows a gelatin capsule containing the balloon 100 and part of the catheter 200, the capsule dissolves rapidly in the intragastric environment. Filler is delivered into the balloon 100 via the extracorporeal end of the catheter 200. The balloon 100 undergoes a transition from an initial decompressed state to an inflated state. Because the diameter of the small orifice 311 is no greater than the outer diameter of the catheter 200, there is a tight, gapless fit between the catheter 200 and the small orifice 311, which ensures an overall seal for the balloon 100 and the self-sealing valve during delivery of the filler so that the filler does not leak. After filling is completed, the catheter 200 is removed. The self-sealing valve upper layer 310 and the self-sealing valve lower layer 320 press tightly against each other under the pressure of the filler in the balloon 100, as shown in FIG. 6. The balloon 100 occupies intragastric volume over a long period of time and thereby attains the weight-loss objective.

FIGS. 7 through 10 depict a balloon system containing a connecting and releasing structure according to another embodiment of the present application. This embodiment differs from the embodiment depicted in FIGS. 3 through 6 in the following respect: the self-sealing valve is not provided with a small orifice, but rather with a distal opening that serves as a catheter connecting port. The structure and fabrication method of a balloon system of this embodiment are described in detail below with reference to FIGS. 7 through 10.

Figure 7:
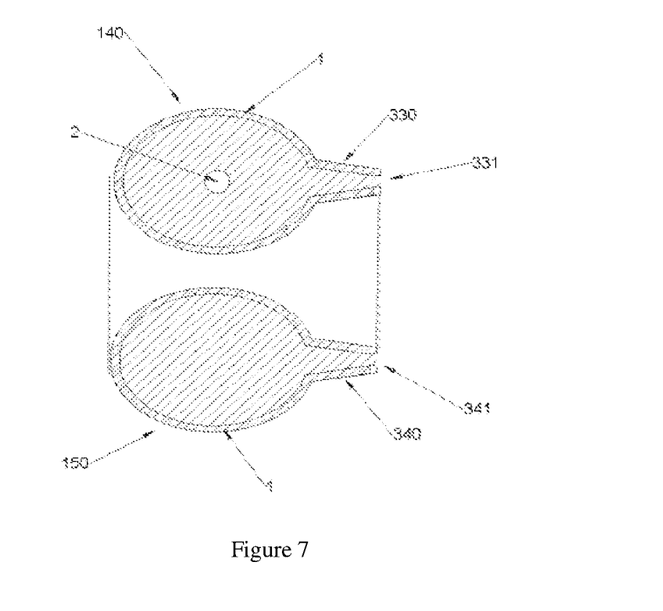
FIG. 7 is a balloon and a self-sealing valve according to another embodiment of the present application and an exploded view of same.

Specifically, FIG. 7 depicts the balloon 100, self-sealing valve 300, and an exploded view thereof. The balloon 100 comprises a balloon upper layer 140 and a balloon lower layer 150. An inversion hole 2 is likewise disposed on the balloon upper layer 140. The self-sealing valve 300 comprises a self-sealing valve upper layer 330 connected to the balloon upper layer 140 and a self-sealing valve lower layer 340 connected to the balloon lower layer 150. Moreover, the self-sealing valve upper layer 330 and the self-sealing valve lower layer 340 are conical. That is, the size of the head 331 (or "free end") of the self-sealing valve upper layer 330 and the head 341 of the self-sealing valve lower layer 340 is smaller than the end which is connected to the balloon. The self-sealing valve upper layer 330 and the balloon upper layer 140 may be formed entirely from the same type of material or may be connected together by bonding or welding different materials. Likewise, the self-sealing valve lower layer 340 and the balloon lower layer 150 may be formed entirely from the same type of material or may be connected together by bonding or welding different materials.

Figure 8:
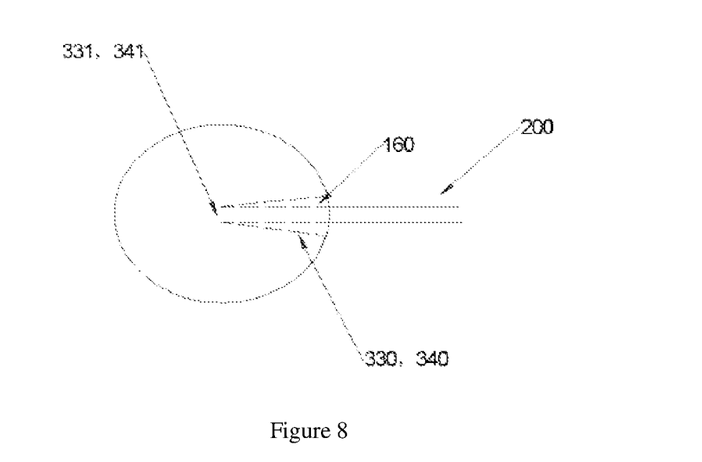
FIG. 8 is a top view of a catheter assembled with the self-sealing valve depicted in FIG. 7.
Figure 9:
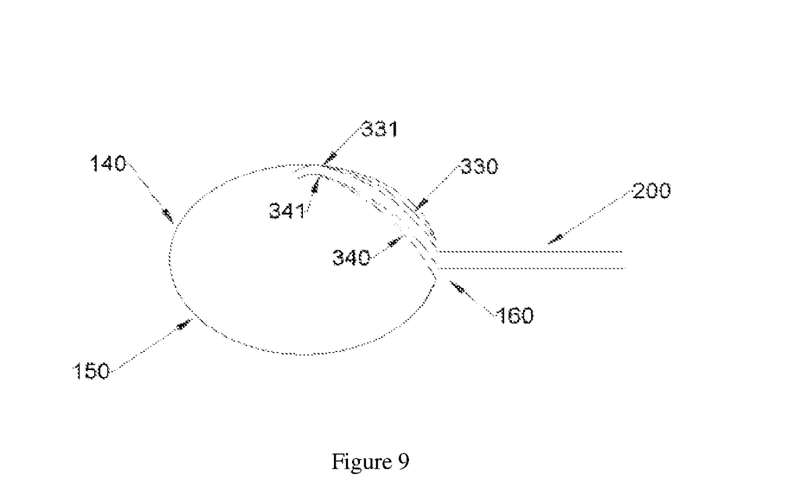
FIG. 9 is a side view of a catheter assembled with the self-sealing valve depicted in FIG. 7.

The balloon upper layer 140 and the self-sealing valve upper layer 330 are combined with the balloon lower layer 150 and the self-sealing valve lower layer 340 by bonding or welding them along their edges 1. However, the head 331 of the self-sealing valve upper layer 330 and the head 341 of the self-sealing valve lower layer 340 are not bonded, and the perimeter of the opening formed by the head 331 of the self-sealing valve upper layer 330 and the head 341 of the self-sealing valve lower layer 340 is no greater than the outer diameter of the catheter 200. After the layers are combined, they are inverted through use of the inversion hole 2 on the balloon upper layer 140. The balloon upper layer 140 and the balloon lower layer 150 form the balloon 100, and the self-sealing valve upper layer 330 and the self-sealing valve lower layer 340 form the self-sealing valve 300, which enters the interior of the balloon 100, as shown in FIG. 8. The distal end or all of the self-sealing valve upper layer 330 is bonded to the inner wall of the balloon 100, as shown in FIGS. 8 and 9. Lastly, the inversion hole 2 on the balloon upper layer 140 is sealed with a patch.

Refer to FIGS. 8 and 9. FIG. 8 is a top view of a catheter assembled with the self-sealing valve of the balloon depicted in FIG. 7, and FIG. 9 is a side view of a catheter assembled with the self-sealing valve of the balloon depicted in FIG. 7. The catheter 200 passes from outside the balloon 100 into the passage lumen 160 between the self-sealing valve upper layer 330 and the self-sealing valve lower layer 340 and passes out from the opening formed by the head 331 of the self-sealing valve upper layer 330 and the head 341 of the self-sealing valve lower layer 340 into the interior of the balloon 100.

Figure 10:
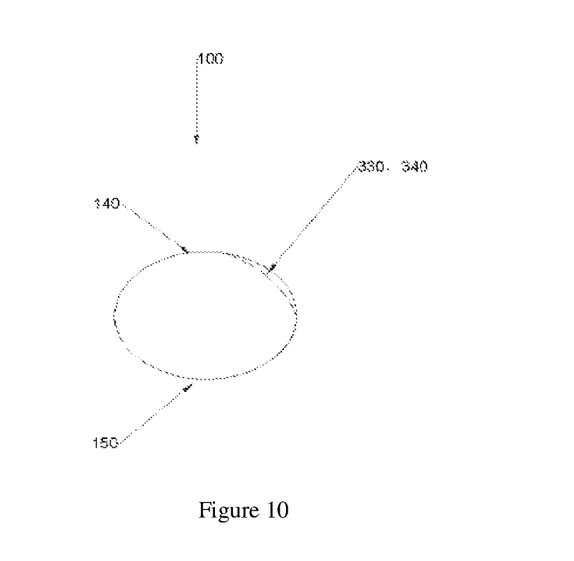
FIG. 10 is a side view of the balloon after the catheter was removed from the self-sealing valve depicted in FIG. 7.

The intragastric balloon according to the present embodiment is used as follows: after the patient swallows a gelatin capsule containing the balloon 100 and part of the catheter 200, the capsule dissolves rapidly in the intragastric environment. Filler is delivered into the balloon 100 via the extracorporeal end of the catheter 200. The balloon 100 undergoes a transition from an initial decompressed state to an inflated state. Because the perimeter of the opening formed by the head 331 of the self-sealing valve upper layer 330 and the head 341 of the self-sealing valve lower layer 340 is no greater than the outer diameter of the catheter 200, there is a tight, gapless fit between the catheter 200 on the one hand and the head 331 of the self-sealing valve upper layer 330 and the head 341 of the self-sealing valve lower layer 340 on the other hand, which ensures an overall seal for the balloon 100 and the self-sealing valve 300 during delivery of the filler so that the filler does not leak. After filling is completed, the catheter 200 is removed. The self-sealing valve upper layer 330 and the self-sealing valve lower layer 340 press tightly against each other under the pressure of the filler in the balloon 100, as shown in FIG. 10. The balloon 100 occupies intragastric volume over a long period of time and thereby attains the weight-loss objective.

According to the connecting and releasing structure of the present application, the self-sealing valve is completely or partially bonded to the inner wall of the balloon. When the catheter is removed after delivery of a filler, the self-sealing valve is not pulled out of the balloon, and thus leakage of the filler can be prevented. In addition, the perimeter of a small orifice in a side wall of the self-sealing valve or the perimeter of the cross-section of the distal end thereof is not greater than the outer diameter of the catheter, and therefore, no leakage occurs when the balloon is full of filler. In addition, the perimeters of cross-sections of the self-sealing valve may differ and increase gradually or stepwise from distal to proximal, thus facilitating the insertion and removal of the catheter.

The invention claimed is:

1. A connecting and releasing system comprising:
a catheter, a self-sealing valve and a balloon,
wherein the self-sealing valve is positioned inside the balloon,
wherein the balloon comprises a balloon upper layer, a balloon lower layer, and an inversion hole disposed on the balloon upper layer,
wherein the self-sealing valve comprises a catheter connecting port, an upper structure comprising a self-sealing valve upper layer connected to the balloon upper layer and a lower structure comprising a self-sealing valve lower layer connected to the balloon lower layer,
wherein the self-sealing valve:
receives the catheter passing through the catheter connecting port;
is sealedly connected to the catheter; and
is wholly or partially secured to an inner wall of the balloon,
wherein the self-sealing valve further comprises a passage lumen positioned in an interior of the balloon; a first distal end of the self-sealing valve is sealedly connected to an opening on the balloon; and the catheter enters the self-sealing valve from the first distal end, exits the catheter connecting port, and enters the interior of the balloon,
wherein the catheter connecting port is disposed in an orifice on at least one side wall of the self-sealing valve, and a diameter of the orifice is not greater than an outer diameter of the catheter, and
wherein an entirety of the self-sealing valve lower layer is bonded to an inner wall of the balloon lower layer.

2. The connecting and releasing system according to claim 1, wherein the first distal end of the self-sealing valve is bonded to the inner wall of the balloon.

3. The connecting and releasing system according to claim 1, wherein:
the self-sealing valve upper layer comprises the orifice;
the upper structure of the self-sealing valve is connected to the lower structure of the self-sealing valve along respective edges to form an integral structure;
the inversion hole is configured such that the integral structure is invertible through the inversion hole;
the balloon upper layer and the balloon lower layer form the balloon, and the self-sealing valve upper layer and the self-sealing valve lower layer form the self-sealing valve positioned inside the balloon; and
the inversion hole on the balloon upper layer is sealed with a patch.

4. The connecting and releasing system according to claim 3, wherein a first distal end of the self-sealing valve upper layer is bonded to an inner wall of the balloon upper layer.

5. The connecting and releasing system according to claim 3, wherein the self-sealing valve upper layer and the balloon upper layer are formed from the same type of material or are connected together by bonding or welding different materials.

6. The connecting and releasing system according to claim 3, wherein the self-sealing valve lower layer and the balloon lower layer are formed from the same type of material or are connected together by bonding or welding different materials.

7. A method for fabricating the connecting and releasing system according to claim 1 comprising:
providing the balloon upper layer, the balloon lower layer, the upper structure, and the lower structure;
disposing the inversion hole on the balloon upper layer;
opening the orifice on the self-sealing valve upper layer, wherein a diameter of the orifice is not greater than the outer diameter of the catheter;
connecting the upper structure to the lower structure along respective edges to form an integral structure;
inverting the integral structure through the inversion hole such that the balloon upper layer and the balloon lower layer forms the balloon, and the self-sealing valve upper layer and the self-sealing valve lower layer forms the self-sealing valve positioned inside the balloon;
bonding an entirety of the self-sealing valve lower layer to the inner wall of the balloon lower layer;
bonding a distal end or an entirety of the self-sealing valve upper layer to an inside wall of the balloon upper layer; and
sealing the inversion hole on the balloon upper layer with a patch.

8. The method according to claim 7, wherein the upper structure and the lower structure are connected by bonding or welding along respective edges.

9. The method according to claim 7, wherein the distal end of the self-sealing valve upper layer is bonded to the inner wall of the balloon.

10. The method according to claim 9, wherein the self-sealing valve is connected to the balloon by bonding or welding.

11. The connecting and releasing system according to claim 1, wherein the connecting and releasing system is an intragastric connecting and releasing system.

12. The connecting and releasing system according to claim 1, wherein the connecting and releasing system is a skin expansion connecting and releasing system.

* * * * *